United States Patent
Schwarz et al.

(10) Patent No.: US 6,388,109 B1
(45) Date of Patent: May 14, 2002

(54) 14,15-CYCLOPROPANO STEROIDS OF THE 19-NORANDROSTANE SERIES, METHOD FOR THE PRODUCTION THEREOF AND PHARMACEUTICAL PREPARATIONS CONTAINING SAID COMPOUNDS

(75) Inventors: Sigfrid Schwarz; Gerd Schubert; Sven Ring, all of Jena; Walter Elger, Berlin; Birgitt Schneider, Jena; Günter Kaufmann, Jena; Lothar Sobek, Jena, all of (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/719,910
(22) PCT Filed: Jun. 18, 1999
(86) PCT No.: PCT/DE99/01795
  § 371 Date: Dec. 20, 2000
  § 102(e) Date: Dec. 20, 2000
(87) PCT Pub. No.: WO99/67276
  PCT Pub. Date: Dec. 29, 1999

(30) Foreign Application Priority Data

Jun. 22, 1998 (DE) .......................................... 198 27 522

(51) Int. Cl.[7] .............................. C07J 53/00; C07J 3/00; C07J 1/00; A61K 31/56
(52) U.S. Cl. ....................... 552/525; 514/182; 514/172; 514/173; 514/174; 552/508; 552/610; 552/523; 552/623
(58) Field of Search .................. 552/508, 523, 552/525, 623, 500; 514/172, 173, 174, 182

(56) References Cited

FOREIGN PATENT DOCUMENTS

EP 768 316 4/1997

OTHER PUBLICATIONS

Oettel et al: Pharmazie vol. 48, No. 7, Jul. 1993, pp. 541–545.
Avery et al: Steroids: Structure, Function and Regulation, vol. 55, No. 2, Feb. 1990; pp 59–64.
Berti et al: Arzneimttel Forschung. Drug Research, vol. 36. No. 9, Sep. 1986 . Pp 1396–1371.
Berti et al: Arzneimttel forschung. Drug Research, vol. 36 No. 9, Sep. 1986; pp. 1372–1374.
Derman RJ: Andro. Disord. (1995) 301–323 (Raven Publishers, NY, N.Y.).

*Primary Examiner*—Sabiha Qazi
(74) *Attorney, Agent, or Firm*—Millen, White, Zelano & Branigan, P.C.

(57) ABSTRACT

Described are new 14,15-cyclopropano steroids of the 19-norandrostane series of general formula (I) and their pharmaceutically acceptable salts, a process for their production and pharmaceutical preparations that contain these compounds. The compounds are distinguished by hormonal (gestagenic and/or androgenic) activity.

(1)

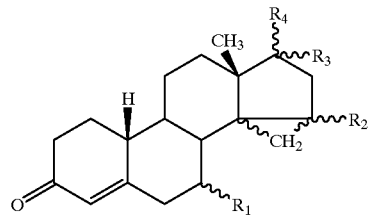

5 Claims, No Drawings

14,15-CYCLOPROPANO STEROIDS OF THE 19-NORANDROSTANE SERIES, METHOD FOR THE PRODUCTION THEREOF AND PHARMACEUTICAL PREPARATIONS CONTAINING SAID COMPOUNDS

This application is a 371 of PCT/DE99/01795 filed on Jun. 18, 1999 which claims priority of DE 198 27 5226 of Jun. 11, 1998.

DESCRIPTION

The invention relates to new 14,15-cyclopropano steroids of the 19-norandrostane series, their production and pharmaceutical preparations that contain these compounds.

14,15-Cyclopropano steroids of the 19-norandrostane series of general formula I

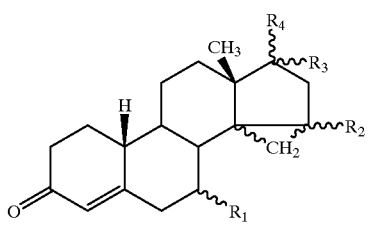

Formula I as described.

In general formula I, $R_1$ is a hydrogen atom or an alkyl radical with 1–9 carbon atoms, $R_2$ stands for a hydrogen atom or a methyl group, $R_3$ and $R_4$, independently of one another, stand for a hydrogen atom, for a hydroxy group, for an acyloxy group —O—CO—$R_5$ with $R_5$ standing for 1–10 carbon atoms, for a carbamoyloxy group O—CO—NHR$_6$, with $R_6$ standing for a hydrogen atom, an alkyl or aryl radical with 1–5 carbon atoms in each case, for a sulfamoyloxy group —O—SO$_2$—NR$_7$R$_8$ with $R_7$ and $R_8$, independently of one another, in each case standing for a hydrogen atom, an alkyl group with 1 to 5 carbon atoms or together with the nitrogen atom for a pyrrolidino, piperidino or morpholino group, for a grouping —CH$_2$R$_9$ with $R_9$ standing for a hydroxy group, an alkyloxy group with 1–5 carbon atoms, a chlorine or bromine atom, an azido, nitrilo or thiocyano group or for a grouping —SR$_{10}$ with $R_{10}$ standing for an alkyl group with 1–5 carbon atoms, or $R_3$ and $R_4$ together stand for an oxo group, or $R_3$ and $R_4$, with the inclusion of C-17, form a spirooxirane or a 2,2-dimethyl-1,3-dioxolane, and the 14,15-cyclopropane ring is arranged either in α- or β-position, whereby $R_2$ is an α-position, if the cyclopropane ring is in β-position and vice versa.

The compounds according to the invention, the new 14,15-cyclopropano steroids of the 19-norandrostane series, have not yet been described. Their biological action is still unknown.

The object of this invention is to make available 14,15-cyclopropano steroids of the 19-norandrostane series of general formula

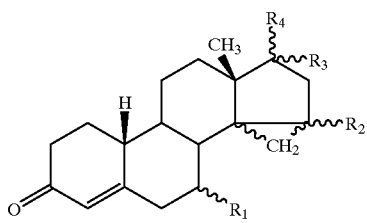

Formula I and their pharmaceutically acceptable salts as well as a process for their production.

Another object is to make available pharmaceutical preparations that contain at least one compound of general formula I or their pharmaceutically acceptable salts.

In general formula I

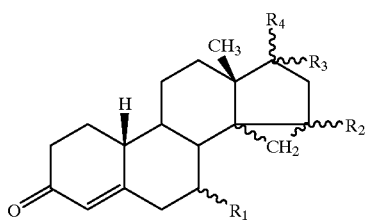

Formula I $R_1$ is a hydrogen atom or an alkyl radical with 1–9 carbon atoms, $R_2$ stands for a hydrogen atom or a methyl group, $R_3$ and $R_4$, independently of one another, stand for a hydrogen atom, for a hydroxy group, for an acyloxy group —O—CO—$R_5$ with $R_5$ standing for 1–10 carbon atoms, for a carbamoyloxy group —O—CO—NHR$_6$, with $R_6$ standing for a hydrogen atom, an alkyl or aryl radical with 1–5 carbon atoms in each case, for a sulfamoyloxy group —O—SO$_2$—NR$_7$R$_8$ with $R_7$ and $R_8$, independently of one another, in each case standing for a hydrogen atom, an alkyl group with 1 to 5 carbon atoms or together with the nitrogen atom for a pyrrolidino, piperidino or morpholino group, for a grouping —CH$_2$R$_9$ with $R_9$ standing for a hydroxy group, an alkyloxy group with 1–5C atoms, a chlorine or bromine atom, an azido, nitrilo or thiocyano group or for a grouping —SR$_{10}$ with $R_{10}$ standing for an alkyl group with 1–5 carbon atoms, or $R_3$ and $R_4$ together stand for an oxo group, or $R_3$ and $R_4$, with the inclusion of C-17, form a spirooxirane or a 2,2-dimethyl-1,3-dioxolane, and the 14,15-cyclopropane ring is arranged either in α- or β-position, whereby $R_2$ is in α-position, if the cyclopropane ring is in β-position and vice versa.

Most preferred are

17β-Hydroxy-14α,15α-methylenestr-4-en-3-one (J 1129),

17α-hydroxy-14α,15α-methylenestr-4-en-3-one,

17β-hydroxy-15β-methyl-14α,15α-methylenestr-4-en-3-one,

17β-hydroxy-15α-methyl-14β,15β-methylenestr-4-en-3-one,

17β-hydroxy-17α-hydroxymethyl-14α,15α-methylenestr-4-en-3-one,

17α-methoxy-17β-methyloxymethyl-14α,15α-methylenestr-4-en-3-one,

17β-hydroxy-7α-methyl-14α,15α-methylenestr-4-en-3-one, 17,20-isopropylidenedioxy-14α,15α-methylene-19,21-bis-nor-17α-pregn-4-en-3-one, 3-oxo-14α,15α-methylenestr-4-en-17β-yl-sulfamate, 3-oxo-14α,15α-methylenestr-4-en-17β-yl-n-butanoate, 17β-hydroxy-17α-methyloxymethyl-14β,15β-methylenestr-4-en-3-one (J 1222), 17α-ethylthiomethyl-17β-hydroxy-14β,15β-methylenestr-4-en-3-one (J 1411), 17α-chloromethyl-17β-hydroxy-14β,15β-methylenestr-4-en-3-one (J 1364), 17α-azidomethyl-17β-hydroxy-14β,15β-methylenestr-4-en-3-one (J 1370), 17α-bromomethyl-17β-hydroxy-14β,15β-ethylenestr-4-en-3-one (J 1424), 17β-hydroxy-17α-rhodanomethyl-14β,15β-methylenestr-4-en-3-one (J 1470), 17α-cyanomethyl-17β-hydroxy-14β,15β-methylenestr-4-en-3-one (J 1517).

The invention also relates to a process for the production of the compounds according to general formula I and their pharmaceutically acceptable salts, which is characterized in that a compound of general formula II

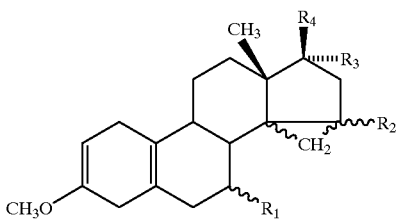

Formula II in which $R_1$, $R_2$, $R_3$ and $R_5$ have the above-indicated meaning, is produced by enol ether cleavage in a way that is known in the art.

The enol ether cleavage is performed by the action of strong acids, such as sulfuric acid, hydrochloric acid or organic sulfonic acids, on the compounds of general formula I that are dissolved in a suitable organic solvent.

Subjects of this invention are pharmaceutical substances for oral, rectal, subcutaneous, intravenous or intramuscular use, which together with the commonly used vehicles and diluents can contain at least one compound of general formula I or its acid addition salts as an active ingredient.

Pharmaceutical preparations of the invention are produced with the commonly used solid or liquid vehicles and/or diluents and the generally commonly used adjuvants corresponding to the desired type of administration in a suitable dosage and in a way that is known in the art. In the case of a preferred oral form for dispensing, preferably tablets, film tablets, coated tablets, capsules, pills, powders, solutions or suspensions are also prepared as a depot form.

In addition, parenteral dosage forms such as injection solutions or else suppositories are also considered.

Dosage forms as tablets can be obtained by, for example, mixing the active ingredient with known adjuvants, such as dextrose, sugar, sorbitol, mannitol, polyvinylpyrrolidone, explosives such as corn starch or alginic acid, binders such as starch or gelatin, lubricants such as magnesium stearate or talc and/or agents that can achieve a depot effect, such as carboxylpolymethylene, carboxymethyl cellulose, cellulose acetate phthalate or polyvinyl acetate. The tablets can also consist of several layers.

Coated tablets can be prepared analogously by coating cores that are produced analogously to the tablets with agents that are commonly used in tablet coatings, for example polyvinylpyrrolidone or shellac, gum arabic, talc, titanium dioxide or sugar. In this case, the coated tablet shell can also consist of several layers, whereby for example, the above-mentioned adjuvants are used.

To improve the taste, the solutions or suspensions with the active ingredient according to the invention can be mixed with substances such as saccharin, cyclamate or sugar and/or with flavoring substances, such as vanillin or orange extract. In addition, they can be mixed with suspension adjuvants, such as sodium carboxymethyl cellulose or preservatives such as p-hydroxybenzoic acid.

The preparation of capsules can be carried out by mixing a pharmaceutical substance with vehicles such as lactose or sorbitol, which then are introduced into the capsules.

The production of suppositories is preferably carried out by mixing the active ingredient with suitable vehicles, such as neutral fats or polyethylene glycols or derivatives thereof.

In addition, the pharmaceutical preparation forms can be percutaneous preparation forms, e.g., transdermal therapeutic systems (TS) or gels, sprays or ointments or intranasal preparation forms such as nose spray or nose drops.

The 14,15-cyclopropano steroids of the 19-norandrostane series of general formula I according to the invention are hormonal (gestagenic- and/or androgenic-acting) compounds.

Thus, for example, the compound of general formula I—in which $R_1$ and $R_2$ in each case represent a hydrogen atom, $R_3$ means an α-position methyloxymethyl group and $R^4$ means a β-position hydroxy group and the cyclopropano group is arrange din β-position—17β-hydroxy-17α-methyloxymethyl-14β,15β-methylenestr-4-en-3-one (J 1222), is just as effective in the pregnancy maintenance test in mice as the gestagen norethisterone acetate that is used worldwide for oral contraception.

Another example is the compound of general formula I—in which $R_1$ and $R_2$ in each case represent a hydrogen atom, $R_3$ represents an α-position hydrogen atom, $R_4$ stands for a β-position hydroxy group, and the cyclopropane ring is in α-position—17β-hydroxy-14,α,15α-methylenestr-4-en-3-one (J 1129), which in the same test has an approximately 50-fold stronger gestagenic action in comparison to the reference substance norethisterone acetate.

While the substance 17β-hydroxy-17α-methyloxymethyl-14β,15β-methylenestr-4-en-3-one (J 1222) with 52±4% binds to the progesterone receptor of the rabbit uterus (reference substance: progesterone), there is virtually no affinity to the androgen receptor of the rat prostate (reference substance: 17β-hydroxy-17α-methyl-estra-4,9,11-trien-3-one; R 1881).

17β-Hydroxy-14α,15α-methylenestr-4-en-3-one (J 1129), however, shows a 59±7% binding to the androgen receptor, which corresponds to the binding affinity of the naturally occurring male sex hormone testosterone, and a 42±5% binding to the progesterone receptor.

Another example is the compound of general formula I—in which $R_1$ and $R_2$ in each case represent a hydrogen atom, $R_3$ means an α-position chloromethyl group, R4 stands for a β-position hydroxy group, and the cyclopropane ring is in β-position—17α-chloromethyl-17β-hydroxy-14β, 15β-methylenestr-4-en-3-one (Code J 1364), which binds with 710±80% to the progesterone receptor of the rabbit uterus (reference substance: progesterone).

In the compounds of general formula I according to the invention, these test results open up many possibilities for birth control in men and women, hormone replacement therapy in men and women, or the treatment or hormonally produced diseases in men and women, such as, for example, endometriosis, breast cancer or hypogonadism.

The compounds of general formula I according to the invention are to be explained in more detail in the examples below, but are not limited thereto.

EXAMPLE 1

17α-Ethylthiomethyl-17β-hydroxy-14β,15β-methylenestr-4-en-3-one 500 mg of 17(S)-3-methoxy-17-spiroepoxy-14β,15β-methylenestra-2,5(10)-diene is heated to 80° C. in 10 ml of DMSO with 270 mg of sodium ethyl thiolate for 4 hours. It is poured into aqueous sodium chloride solution, the brown precipitate is suctioned off and washed neutral. It is dissolved with actone from the frit, and the solution is concentrated by evaporation under a vacuum. A brown oil, which is purified by preparative layer chromatography on silica gel $PF_{254+366\ nm}$ (MERCK AG) with the mobile solvent mixture of toluene/acetone 50:1, remains.

225 mg of 17α-ethylthiomethyl-3-methoxy-17β-hydroxy-14β,15β-methylenestra-2,5(10-diene is reacted in 3.0 ml of dimethylformamide with 0.3 ml of HCl (concentrated) within 1 hour. After aqueous $NaHCO_3$ solution is added, it is neutralized, extracted with $CH_2Cl_2$, the organic phase is washed neutral, dried on sodium sulfate and evaporated under a vacuum. An oil is obtained that is purified by preparative layer chromatography on silica gel $PF_{254+366\ nm}$ (MERCK AG) with the mobile solvent mixture of toluene/acetone 10:1.

After recrystallization from ethanol, 17α-ethylthiomethyl-17β-hydroxy-14β,15β-methylenestr-4-en-3-one is obtained.

Flash point: 92–98° C.; $^1$H-NMR (CDCl$_3$/TMS): 0.47 (2H, m, 14β,15β-CH$_2$), 1.07 (3H, s, H$_{18}$); 1.28 (3H, t, SCH$_2$CH$_3$), 2.52 (2H, q, 14.7 Hz, 7.5 Hz, SCH$_2$), 2.62 and 2.78 (2H, 2d, 12.6 Hz, 17αCH$_2$S—); 2.89 (1H, s, OH), 5.81 (1H, s, H$_4$); after TAI: 0.55 (2H, m, 14β,15β-CH$_2$), 1.21 (3H, t, SCH$_2$CH$_3$), 1.34 (3H, s, H$_{18}$), 2.46 (2H, q, 7.5 Hz, 14.7 Hz, SCH$_2$), 2.82 and 3.00 (2H, 2d, 13.2 Hz, 17α CH$_2$S—); 5.81 (1H, s, H$_4$); 8.21 (s, NHCO) ppm.

EXAMPLE 2

17α-Chloromethyl-17β-hydroxy-14β,15β-methylenestr-4-en-3-one (J 1364)

625 mg of 17(S)-3-methoxy-17-spiroepoxy-14β,15β-methylenestra-2,5(10)-diene is dissolved in 10 ml of DMF and mixed with 1 ml of HCl (concentrated at room temperature. It is stirred for 1.5 hours, poured into ice water, the deposited precipitate is suctioned off, washed neutral and air-dried. The crude product is purified by preparative layer chromatography on silica gel $PF_{254+366\ nm}$ (MERCK AG) with the mobile solvent mixture of toluene/acetone 15:1.

After recrystallization from acetone, 17α-chloromethyl-17β-hydroxy-14β,15β-methylenestr-4-en-3-one is obtained.

Flash point: 177–179° C.; $α_D$=+67° (CHCl$_3$), $^1$H-NMR (CDCl$_3$/TMS+TAI); 0.48 (2H, m, 14β,15β-CH$_2$), 1.34 (3H, s, H$_{18}$); 2.15 (1H, s, OH), 3.56 and 3.67 (2H, 2d, 8.4 Hz, 17α-CH$_2$Cl); 5.79 (1H, s, H$_4$) ppm.

EXAMPLE 3

17α-Azidomethyl-17β-hydroxy-14β,15β-methylenestr-4-en-3-one 550 mg of 17(S)-3-methoxy-17-spiroepoxy-14β,15β-methylenestra-2,5(10)-diene is heated to 100° C. in 35 ml of ethylene glycol with 2.6 g of sodium azide for 6 hours. It is poured into ice water, extracted with $CH_2Cl_2$, washed neutral, dried on sodium sulfate, and the solution is concentrated by evaporation under a vacuum. The crude product is purified by preparative layer chromatography on silica gel $PF_{254+366\ nm}$ (MERCK AG) with the mobile solvent mixture of toluene/acetone 50:1). After recrystallization from acetone, 17α-azidomethyl-17β-hydroxy-14β,15β-methylenestra-2,5 (10)-3-methyl ether is obtained as crystals with a melting point of 138–143° C.

285 mg of 17α-azidomethyl-17β-hydroxy-3-methoxy-14β,15β-methylenestra-2,5(10)-diene is reacted in 4 ml of dimethylformamide with 0.4 ml of HCl (concentrated) within 2 hours. After aqueous $NaHCO_3$ solution is added, it is neutralized, extracted with $CH_2Cl_2$, the organic phase is washed neutral, dried on sodium sulfate and evaporated under a vacuum. A yellow oil that is purified by preparative layer chromatography on silica gel $PF_{254+366\ nm}$ (MERCK AG) with the mobile solvent mixture of toluene/acetone 20:1 is obtained.

After recrystallization from tert-butyl methyl ether/hexane, 17α-azidomethyl-17β-hydroxy-14β,15β-methylenestr-4-en-3-one is obtained.

Flash point: 160–163° C.; $α_D$=+84° (CHCl$_3$), $^1$H-NMR (CDCl$_3$/TMS); 0.54 (2H, m, 14β,15β-CH$_2$), 1.28 (3H, s, H$_{18}$); 2.03 (1H, s, OH), 3.34 and 3.46 (2H, 2d, 12.0 Hz, CH$_2$N$_3$), 5.81 (s, 1H, H$_4$) ppm.

EXAMPLE 4

17β-Hydroxy-17α-(methoxymethyl)-14β,15β-methylenestr-4-en-3-one (J 1222)

3.42 g of 17α-(methoxymethyl)-3-methoxy-14β,15β-methylenestra-2,5(10)-dien-17β-ol is suspended in 70 ml of MeOH and mixed with 3.4 ml of HCl (concentrated at room temperature. It is stirred for 2 hours, mixed with 50 ml of water and neutralized with aqueous bicarbonate solution. The deposited precipitate is suctioned off, washed neutral and air-dried. Yield: 3.19 g of crude product. Purification by column chromatography on silica gel (0.063–0.2 mm MERCK AG) with a toluene/acetone gradient.

After recrystallization from isopropanol, 2.4 g of 17β-hydroxy-17α-(methoxymethyl)-14β,15β-methylenestr-4-en-3-one is obtained.

Flash point: 113–115° C. (isopropanol); $α_D$=+49° (CHCl$_3$), $^1$H-NMR (CDCl$_3$/TMS); 0.47 (2H, m, 14β,15β-CH$_2$), 1.10 (3H, s, H$_{18}$); 2.71 (1H, s, OH), 3.17 and 3.44 (2H, 2d, 9.0 Hz, 17α-CH$_2$OCH$_3$); 3.33 (1H, s, OCH$_3$), 5.81 (1H, s, H$_4$) ppm.

EXAMPLE 5

17β-Hydroxy-14α,15α-methylenestr-4-en-3-one (J 1129)

A solution that consists of 2 g of 17β-hydroxy-14α,15α-methylenestr-5-en-3-one in 95 ml of acetone and 5 ml of 5% aqueous hydrochloric acid is stirred for 2.5 hours at room temperature. Then, 10 ml of saturated aqueous sodium bicarbonate solution and 200 ml of water are added in succession. This solution is concentrated by evaporation in a vacuum rotary evaporator, whereby crystallization is used. The crystals are filtered off, dried, dissolved in acetone and applied to a silica gel column (0.063–0.2 mm, Merck). Chromatography with cyclohexane ethyl acetate 7:3 (v/v) as an eluant yields 17β-hydroxy-14α,15α-methylenestr-4-en-3-one.

Flash point 168–170° C.; $[\alpha]_D^{20}$+67° (pyridine); $^1$H-NMR (CDCl$_3$/TMS+TAI): 0.265 (1H, dd, 5.8 Hz, 3.2 Hz, 14α,15α-CH$_2$); 0.338 (1H, t, 7 Hz, 14α,15α-CH$_2$); 1.13 (3H, s, H$_{18}$); 4.58 (1H, dd, H$_{17\alpha}$); 5.82 (s, H$_4$); 8.41 (s, NH) ppm.

EXAMPLE 6

17α-Hydroxy-14α,15α-methylenestr-4-en-3-one

17α-Hydroxy-14α,15α-methylenestr-5-en-3-one is treated with hydrochloric acid in acetone analogously to Example 5, and the product is subjected to chromatography, whereby 17α-hydroxy-14α,15α-methylenestr-04-en-3-one is obtained.

$^1$H-NMR (CDCl$_3$/TMS+TAI); 0.39 (1H, dd, 7.2 Hz, 4.9 Hz, 14α,15α-CH$_2$); 0.67 (1H, dd, 4.9 Hz, 2.8 Hz, 14α,15α-CH$_2$); 1.12 (3H, s, H$_{18}$); (4.96, 1H, d, 6.1 Hz, H$_{17\beta}$); 5.81 (s, H$_4$); 8.42 (s, NH) ppm.

EXAMPLE 7

17β-Hydroxy-17α-hydroxymethyl-14α,15α-methylenestr-4-en-3-one

17β-Hydroxy-17α-hydroxymethyl-14α,15α-methylenestr-5-en-3-one is treated with hydrochloric acid in acetone analogously to Example 5, and the product is subjected to chromatography, whereby 17β-hydroxy-17α-hydroxymethyl-14α,15α-methylenestr-4-en-3-one is obtained.

$^1$H-NMR (CDCl$_3$TMS+TAI): 0.26 (1H, dd, 6.8 Hz, 2.0 Hz, 14α,15α-CH$_2$); 0.51 (1H, t, 6.8 Hz, 14α,15α-CH$_2$); 1.26 (3H, s, H$_{18}$); 4.58, 4.93 (2H, AB, 12.2 Hz, CH$_2$O); 5.82 (1H, t, 2.2 Hz, H$_4$); 8.44 (1H, s, NH); 8.52 (1H, s, NH) ppm.

EXAMPLE 8

17α-Methoxy-17β-methoxymethyl-14α,15α-methylenestr-4-en-3-one

17α-Methoxy-17β-methoxymethyl-14α,15α-methylenestr-5-en-3-one is treated with hydrochloric acid in acetone analogously to Example 5, and the product is subjected to chromatography, whereby 17α-methoxy-17β-methoxymethyl-14α,15α-methylenestr-4-en-3-one is obtained.

$^1$H-NMR (CDCl$_3$/TMS): 0.18 (1H, m 14α,15α-CH$_2$); 0.954 (1H, t, 3.3 Hz, 14α,15α-CH$_2$); 1.11 (3H, s, H$_{18}$); 3.15 (3H, s, OCH$_3$); 3.31 (3H, s, OCH$_3$); 3.26, 3.52 (2H, AB, 11.2 Hz, CH$_2$O), 5.80 (1H, t, 1 Hz, H$_4$) ppm.

EXAMPLE 9

17,20-Isopropylidenedioxy-14α,15α-methylene-19,21-bis-nor-17α-pregn-4-en-3-one 17,20-Isopropylidenedioxy-14α,15α-methylene-19,21-bis-nor-17α-pregna-5-en-3-one is treated with hydrochloric acid in acetone analogously to Example 5, and the product is subjected to chromatography, whereby 17,20-isopropylidenedioxy-14α,15α-methylene-19,21-bis-nor-17α-pregn-4-en-3-one is obtained.

$^1$H-NMR (CDCl$_3$/TMS): −0.27 (1H, m, 14α,15α-CH$_2$); 0.32 (t, 14α,15α-CH$_2$); 1.14 (3H, s, H$_{18}$); 1.30 (3H, s, OCH$_3$); 1.37 (3H, s, OCH$_3$); 3.50, 4.07 (2H, AB, 8.5 Hz, CH$_2$O), 5.81 (1H, t, 2.2 Hz, H$_4$) ppm.

EXAMPLE 10

17α-Bromomethyl-17β-hydroxy-14β,15β-methylenestr-4-en-3-one 666 mg of 17(S)-spiroepoxy-14β,15β-methylenestra-2,5(10)-diene-3-methyl ether is dissolved in 10 ml of DMF and mixed with 2.5 ml of HBR (48%) at room temperature. It is stirred for 4 hours, poured into ice water, the deposited precipitate is suctioned off, washed neutral and air-dried. The crude product is purified by preparative layer chromatography on silica gel PF$_{254+366\ nm}$ (MERCK AG) with the mobile solvent mixture of toluene/acetone 20:1.

After twice-repeated recrystallization from acetone, 324 mg of 17α-bromomethyl-17β-hydroxy-14β,15β-methylenestr-4-en-3-one is obtained.

Flash point: 143 (dec.) ° C.; $\alpha_D$=+68° (CHCl$_3$), $^1$H-NMR (CDCl$_3$, ppm, TMS); 0.50 (m, 2H, 14β,15β-CH$_2$), 1.15 (s, 3H, H-18); 2.27 (s, 1H, OH), 3.57 (t, 2H, J=10.2 Hz, H-17α-CH$_2$Br); 5.81 (s, 1H, H-4).

EXAMPLE 11

17β-Hydroxy-17α-rhodanomethyl-14β,15β-methylenestr-4-en-3-one 666 mg of 17(S)-spiroepoxy-14β,15β-methylenestra-2,5(10)-diene-3-methyl ether is dissolved in 10 ml of DMF and mixed with 2.5 ml of HBr (48%) at room temperature. It is stirred for 4 hours, poured into ice water, the deposited precipitate is suctioned off, washed neutral and air-dried. The crude product is purified by preparative layer chromatography on silica gel PF$_{254+366\ nm}$ (MERCK AG) with the mobile solvent mixture of toluene/acetone 20:1.

After recrystallization from ethyl acetate and MeOH that is repeated three times, 185 mg of 17β-hydroxy-17α-rhodanomethyl-14β,15β-methylenestr-4-en-3-one is obtained.

Flash point: 168–173° C. (MeOH); $\alpha_D$=+86° (CHCl$_3$), $^1$H-NMR (CDCl$_3$, ppm, TMS); 0.53 (m, 2H, 14β,15β-CH$_2$), 1.11 (s, 3H, H-18); 1.98 (s, 1H, OH), 3.21 (t, 2H, J=10.2 Hz, H-17α-CH$_2$SCN); 5.82 (s, 1H, H-4).

EXAMPLE 12

17α-Cyanomethyl-17β-hydroxy-14β,15β-methylenestr-4-en-3-one 624 mg of 17(S)-spiroepoxy-14β,15β-methylenestra-2,5(10)-diene-3-methyl ether is suspended in 15 ml of ethanol and stirred with 490 mg of sodium cyanide at room temperature until conversion is completed. Then, it is poured into ice water, it is suctioned off, washed neutral and air-dried. The crude product of 17α-cyanomethyl-3-methoxy-14β,15β-methylenestra-2,5(10)-dien-17β-ol is purified by preparative layer chromatography on silica gel PF$_{254+366\ nm}$ (MERCK AG) with the mobile solvent mixture of toluene/acetone 20:1, dissolve din 10 ml of DMF and mixed with 0.5 ml of HCl. After 2 hours, it is poured into ice water, the precipitate is suctioned off and purified by chromatography. The recrystallization of 17α-cyanomethyl-17β-hydroxy-14β,15β-methylenestr-4-en-3-one is carried out from acetone.

Flash point: 244–253° C.; $\alpha_D$=+65° (CHCl$_3$), $^1$H-NMR (CDCl$_3$/TMS); 0.56 (m, 2H, 14β,15β-CH$_2$), 1.17 (s, 3H, H-18); 2.28 (s, 1H, OH), 2.3–2.5 (m, H-17α-CH$_2$CN); 5.82 (s, 1H, H-4).

What is claimed is:

1. A compound of formula I

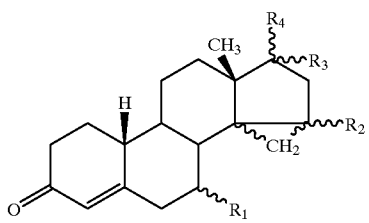

Formula I in which
R₁ is a hydrogen atom or an alkyl radical with 1–9 carbon atoms,
R₂ is a hydrogen atom or a methyl group,
R₃ and R₄, independently of one another, stand for a
  a hydrogen atom,
  for a hydroxy group,
  for an acyloxy group —O—CO—R₅,
    with R₅ standing for an alkyl of 1–10 carbon atoms,
  for a carbamoyloxy group —O—CO—NHR₆,
    with R₆ standing for a hydrogen atom or an alkyl or aryl radical,
  for a sulfamoyloxy group —O—SO₂—NR₇R₈,
    with R₇ and R₈, independently of one another, in each case standing for a hydrogen atom, an alkyl group with 1 to 5 carbon atoms or together with the nitrogen atom for a pyrrolidino, piperidono or morpholino group,
  for a grouping —CH₂R₉ with R₉ standing for a hydroxy group,
    an alkyloxy group with 1–5 carbon atoms, a chlorine or bromine atom, an azido, nitrilo or thiocyano group or for a grouping —SR₁₀
      with R₁₀ standing for an alkyl group with 1–5 carbon atoms,
R₃ and R₄ together stand for an oxo group, or
R₃ and R₄, with C-17, form a spirooxirane or a 2,2-dimethyl-1,3-dioxolane group,
or a pharmaceutically acceptable salt thereof.

2. A compound according to claim 1,
17β-hydroxy-14α,15α-methylenstr-4-en-3-one or a pharmaceutically acceptable salt thereof,
17α-hydroxy-14α,15α-methylenestr-4-en-3-one or a pharmaceutically acceptable salt thereof,
17β-hydroxy-15β-methyl-14α,15α-methylenstr-4-en-3-one or a pharmaceutically acceptable salt thereof,
17β-hydroxy-15α-methyl-14β,15β-methylenestr-4-en-3-one or a pharmaceutically acceptable salt thereof,
17β-hydroxy-17α-hydroxymethyl-14α,15α-methylenestr-4-en-3-one or a pharmaceutically acceptable salt thereof,
17α-methoxy-17β-methoxymethyl-14α,15α-methylenestr-4-en-3-one or a pharmaceutically acceptable salt thereof,
17β-hydroxy-7α-methyl-14α,15α-methylenestr-4-en-3-one or a pharmaceutically acceptable salt thereof,
17,20-isopropylidenedioxy-14α,15α-methylene-19,21-bis-nor-17α-pregn-4-en-3-one or a pharmaceutically acceptable salt thereof,
3-oxo-14α,15α-methylenstr-4-en-17β-yl-sulfamate or a pharmaceutically acceptable salt thereof,
3-oxo-14α,15α-methylenestr-4-en-17β-yl-n-butanoate or a pharmaceutically acceptable salt thereof,
17β-hydroxy-17α-methyloxymethyl-14β-,15β-methylenestr-4-en-3-one or a pharmaceutically acceptable salt thereof,
17α-ethylthiomethyl-17β-hydroxy-14β,15β-methylenestr-4-ene-3-one or a pharmaceutically acceptable salt thereof,
17α-chloromethyl-17β-hydroxy-14β,15β-methylenestr-4-en-3-one or a pharmaceutically acceptable salt thereof,
17α-azidomethyl-17β-hydroxy-14β,15β-methylenestr-4-en-3-one or a pharmaceutically acceptable salt thereof,
17α-bromomethyl-17β-hydroxy-14β,15β-ethylenestr-4-en-3-one or a pharmaceutically acceptable salt thereof,
17β-hydroxy-17α-rhodanomethyl-14β,15β-methylenestr-4-en-3-one or a pharmaceutically acceptable salt thereof or,
17α-cyanomethyl-17β-hydroxy-14β,15β-methylenestr-4-en-3-one or a pharmaceutically acceptable salt thereof.

3. A process for the production of a compound according to claim 1 and its pharmaceutically acceptable salt comprising enol-ether cleaving a corresponding 14,15-cyclopropano-enol ether of the general formula II,

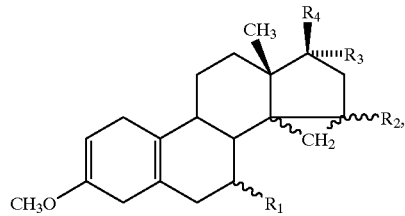

Formula II in which
R₁ is a hydrogen atom or an alkyl radical with 1–9 carbon atoms,
R₂ is a hydrogen atom or a methyl group,
R₃ and R₄, independently of one another, stand for a
  hydrogen atom
  for a hydroxy group,
  for a acyloxy group —O—CO—R₅
    with R₅ standing for an alkyl of 1–10 carbon atoms,
  for a carbamoyloxyl group —O—CO—NHR₆,
    with R₆ standing for a hydrogen atom, or an alkyl or aryl radical,
  for a sulfamoyloxy group —O—SO₂—NR₇R₈,
    with R₇ and R₈, independently of one another, in each case standing for a hydrogen atom, an alkyl group with 1–5 carbon atoms or together with the nitrogen atom for a pyrrolidino, piperidono or morphilino group,
  for a grouping —CH₂R₉ with R₉ standing for a hydroxy group, an alkyloxy group with 1–5 carbon atoms, a chlorine or bromine atom, an azido, nitrilo or thiocyano group or for a grouping —SR₁₀ with R₁₀ standing for an alkyl group with 1–5 carbon atoms,
R₃ and R₄ together stand for an oxo group, or
R₃ and R₄, with C-17, form a spirooxirane or a 2,2-dimethyl-1,3-dioxolane group.

4. A pharmaceutical composition comprising a compound of claim 1 and a pharmaceutically acceptable carrier.

5. A compound of formula I

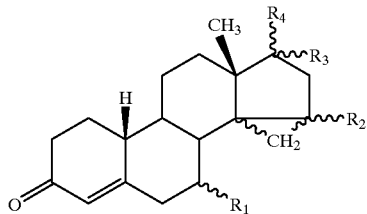

in which
  $R_1$ is a hydrogen atom or an alkyl radical with 1–9 carbon atoms,
  $R_2$ is a hydrogen atom or a methyl group,
  $R_3$ and $R_4$, independently of one another, stand for
    a hydrogen atom,
    for a hydroxy group,
    for an acyloxy group —O—CO—$R_5$,
      with $R_5$ standing for an alkyl of 1–10 carbon atoms,
    for a carbamoyloxy group —O—CO—NH$R_6$,
      with $R_6$ standing for a hydrogen atom or an alkyl radical,
    for a sulfamoyloxy group —O—SO$_2$—N$R_7R_8$,
      with $R_7$ and $R_8$, independently of one another, in each case standing for a hydrogen atom, an alkyl group with 1 to 5 carbon atoms or together with the nitrogen atom for a pyrrolidino, piperidono or morpholino group,
    for a grouping —CH$_2R_9$ with $R_9$ standing for a hydroxy group,
    an alkyloxy group with 1–5 carbon atoms, a chlorine or bromine atom, an azido, nitrilo or thiocyano group or for a grouping —S$R_{10}$
      with $R_{10}$ standing for an alkyl group with 1–5 carbon atoms,
  $R_3$ and $R_4$ together stand for an oxo group, or
  $R_3$ and $R_4$, with C-17, form a spirooxirane or a 2,2-dimethyl-1,3-dioxolane group,
or a pharmaceutically acceptable salt thereof.

* * * * *

UNITED STATES PATENT AND TRADEMARK OFFICE
CERTIFICATE OF CORRECTION

PATENT NO.    : 6,388,109 B1
DATED         : May 14, 2002
INVENTOR(S)   : Schwarz et al.

It is certified that error appears in the above-identified patent and that said Letters Patent is hereby corrected as shown below:

<u>Title page, Item [54] and Column 1, line 1,</u>
Change "14, 15 CYCLOPROPANO STEROIDS" to
-- CYCLOPROPANOSTEROIDS --

<u>Column 9,</u>
Line 32, change "piperidono" to -- piperidino --.
Lines 46, 50 and 66, change "methylenstr" to -- methylenestr --.

<u>Column 10,</u>
Line 55, change "piperidono" to -- piperidino --.

Signed and Sealed this

Twenty-sixth Day of August, 2003

JAMES E. ROGAN
*Director of the United States Patent and Trademark Office*